(12) United States Patent
Ohno et al.

(10) Patent No.: US 8,030,528 B2
(45) Date of Patent: Oct. 4, 2011

(54) PROCESS FOR PRODUCING 1,2,3,4-TETRACHLOROHEXAFLUOROBUTANE

(75) Inventors: Hiromoto Ohno, Minato-ku (JP); Toshio Ohi, Minato-ku (JP)

(73) Assignee: Showa Denko K.K., Tokyo (JP)

( * ) Notice: Subject to any disclaimer, the term of this patent is extended or adjusted under 35 U.S.C. 154(b) by 35 days.

(21) Appl. No.: 12/596,568

(22) PCT Filed: Apr. 14, 2008

(86) PCT No.: PCT/JP2008/057282
§ 371 (c)(1),
(2), (4) Date: Oct. 19, 2009

(87) PCT Pub. No.: WO2008/133086
PCT Pub. Date: Nov. 6, 2008

(65) Prior Publication Data
US 2010/0121118 A1    May 13, 2010

(30) Foreign Application Priority Data

Apr. 20, 2007 (JP) .................................. 2007-111750

(51) Int. Cl.
*C07C 17/00* (2006.01)
(52) U.S. Cl. ....................................................... 570/161
(58) Field of Classification Search ................... 570/161
See application file for complete search history.

(56) References Cited

U.S. PATENT DOCUMENTS 6,203,671 B1    3/2001    Demmin

FOREIGN PATENT DOCUMENTS

| JP | 1-305041 A | 12/1989 |
| JP | 2002-539096 A | 11/2002 |
| JP | 2006-342059 A | 12/2006 |

OTHER PUBLICATIONS

Computer translation of JP 2006-342059, Dec. 21, 2006.*

* cited by examiner

*Primary Examiner* — Jafar Parsa
(74) *Attorney, Agent, or Firm* — Sughrue Mion, PLLC

(57) ABSTRACT

The process for producing a fluorine-containing compound such as 1,2,3,4-tetrachlorohexafluorobutane of the present invention is characterized in that a halogenated hydrocarbon compound such as 1,2,3,4-tetrachlorobutane is brought into contact with fluorine gas in a liquid phase or in a solid-liquid coexistence state in the absence of a solvent and a catalyst. According to the present invention, a fluorine-containing compound is readily produced from a halogenated hydrocarbon compound using neither a reaction solvent nor a reaction catalyst.

6 Claims, No Drawings

PROCESS FOR PRODUCING 1,2,3,4-TETRACHLOROHEXAFLUOROBUTANE

TECHNICAL FIELD

The present invention relates to a process for producing a fluorine-containing compound. More particularly, the present invention relates to a process for efficiently producing a fluorine-containing compound, particularly 1,2,3,4-tetrachlorohexafluorobutane, which is useful as a raw material for synthesizing hexafluoro-1,3-butadiene having been noted as, for example, an etching gas for semiconductors.

BACKGROUND ART 1,2,3,4-Tetrachlorohexafluorobutane is a compound which is important as a raw material for synthesizing hexafluoro-1,3-butadiene having been noted as, for example, a fine processing etching gas for semiconductors.

As a process for producing the 1,2,3,4-tetrachlorohexafluorobutane, the following process has been hitherto known.

(1) Japanese Patent Laid-Open Publication No. 2006-342059 (patent document 1) describes a process for producing 1,2,3,4-tetrachlorohexafluorobutane by bringing a halogenated compound represented by $CClX^1X^2$—$CClX^3$—$CClX^4$—$CClX^5X^6$ (X is a hydrogen atom or a fluorine atom) into contact with fluorine gas in a liquid phase.

In this process, a reaction solvent is used. The patent document 1 describes that perfluoroalkanes, perfluoroethers, perfluoropolyethers, chlorinated fluorinated hydrocarbons and perfluoroalkylamines are used as the reaction solvents.

However, if a reaction solvent is used as above, it is necessary to separate the reaction product from the reaction solvent. Although the separated reaction solvent can be separated from the product, recovered and recycled, it cannot be denied that the operation of separating the reaction solvent is complicated. When 1,2,3,4-tetrachlorohexafluorobutane is used as a reaction solvent, there is an advantage that the separation between the reaction solvent and the product is unnecessary. In this reaction, however, the fluorination reaction is carried out with a low concentration of the reaction raw material diluted with a reaction solvent, so that from the viewpoint of industrially efficient production of a desired product, a problem is left.

As described above, in the conventional process, the reaction solvent is used as an essential component and therefore, there is also a problem that the operation of separating it is extremely complicated.

Patent document 1: Japanese Patent Laid-Open Publication No. 2006-342059

DISCLOSURE OF THE INVENTION

Problem to be Solved by the Invention

The present invention is intended to solve such problems associated with the prior art as mentioned above, and an object thereof is to provide a process for efficiently producing a fluorine-containing compound such as 1,2,3,4-tetrachlorohexafluorobutane which is useful as a raw material for synthesizing hexafluoro-1,3-butadiene having been noted as, for example, an etching gas for semiconductors.

Means to Solve the Problem

In order to solve the above problems, the present inventors have earnestly studied. As a result, they have found a process for inexpensively and economically producing a fluorine-containing compound in a high yield by causing a halogenated hydrocarbon compound to react with fluorine gas in a liquid phase or in a solid-liquid coexistence state in the absence of a solvent and a catalyst, and they have accomplished the present invention.

That is to say, the present invention resides in the following [1] to [10].

[1] A process for producing a fluorine-containing compound, comprising causing a halogenated hydrocarbon compound to react with fluorine gas in a liquid phase or in a solid-liquid coexistence state in the absence of a solvent and a catalyst.

[2] The process for producing a fluorine-containing compound as described in [1], wherein the halogenated hydrocarbon compound is a compound in which plural hydrogen atoms directly bonded to carbon atoms of a hydrocarbon compound of 3 to 6 carbon atoms are replaced with halogen atoms.

[3] The process for producing a fluorine-containing compound as described in [1], wherein the halogenated hydrocarbon compound is 1,2,3,4-tetrachlorobutane and the fluorine-containing compound is 1,2,3,4-tetrachlorohexafluorobutane.

[4] The process for producing a fluorine-containing compound as described in [1], wherein the reaction temperature of the reaction is in the range of –10 to 70° C.

[5] The process for producing a fluorine-containing compound as described in [1], wherein the reaction pressure of the reaction is in the range of 0.1 to 2.0 MPa.

[6] The process for producing a fluorine-containing compound as described in [3], wherein the 1,2,3,4-tetrachlorobutane is mainly obtained by chlorination reaction of 3,4-dichlorobutene-1.

[7] The process for producing a fluorine-containing compound as described in [6], wherein in the 1,2,3,4-tetrachlorobutane obtained by the chlorination reaction of the 3,4-dichlorobutene-1, a dl form which is an optical isomer is contained in an amount of not less than 40% by mass.

[8] The process for producing a fluorine-containing compound as described in [1], wherein the fluorine gas is diluted with a diluent gas and then introduced into a reaction apparatus.

[9] The process for producing a fluorine-containing compound as described in [8], wherein the concentration of the fluorine gas in the diluted fluorine gas is not less than 30% by volume.

[10] The process for producing a fluorine-containing compound as described in [8] or [9], wherein the diluent gas is at least one inert gas selected from the group consisting of nitrogen gas, helium gas, argon gas and neon gas.

Effect of the Invention

According to the present invention, there can be provided a process for efficiently producing a fluorine-containing compound such as 1,2,3,4-tetrachlorohexafluorobutane industrially, safely, economically and advantageously in a high yield, by bringing a halogenated hydrocarbon compound such as 1,2,3,4-tetrachlorobutane into contact with fluorine gas in a liquid phase or in a solid-liquid coexistence state in the absence of a solvent and a catalyst, with formation of a low-boiling component due to C—C cleavage inhibited and a progress of excessive fluorination prevented.

BEST MODE FOR CARRYING OUT THE INVENTION

Preferred embodiments of the present invention are described in detail hereinafter. But it should be understood that the present invention is not limited to those embodiments and that various modifications are possible within the thought and the scope of practice of the present invention.

The production process of the present invention is a process for producing a fluorine-containing compound by bringing a halogenated hydrocarbon compound into contact with fluorine gas in a liquid phase or in a solid-liquid coexistence state using neither a solvent nor a catalyst.

Examples of the halogenated hydrocarbon compound used as a raw material in the present invention include a compound which is a hydrocarbon compound of 3 or more carbon atoms, preferably 3 to 6 carbon atoms, and in which at least one hydrogen atom, preferably plural hydrogen atoms directly bonded to these carbon atoms is replaced with a halogen atom. Examples of such halogenated hydrocarbon compounds include compounds in which a part of hydrogen atoms bonded to carbon atoms of a hydrocarbon compound are replaced with halogen atoms (preferably halogen atoms except for fluorine), such as 1,2,3,4-tetrachlorobutane, 1,2,3,4-tetrabromobutane and 1,2,3,4-tetraiodobutane. These halogenated hydrocarbon compounds can be used alone or in combination.

In the present invention, such a hydrocarbon compound substituted with a halogen atom such as chlorine, bromine or iodine, is used and brought into contact with fluorine gas using neither a reaction solvent nor a reaction catalyst to replace a hydrogen atom bonded to a carbon atom of the halogenated hydrocarbon compound with a fluorine atom, whereby a fluorine-containing compound is produced. In the present invention, as the halogenated hydrocarbon compound used for the above reaction, it is preferable to use a compound in which a part of hydrogen atoms directly bonded to carbon atoms that constitute the hydrocarbon compound are replaced with halogen atoms, particularly chlorine atoms. Such compound is supplied industrially and inexpensively as compared with other halogenated hydrocarbon compounds. And by the use of the compound, a fluorine-containing compound which is a desired substance can be inexpensively produced, and besides, production of a fluorine-containing compound can be readily carried out.

1,2,3,4-Tetrachlorobutane which is a typical example of such compounds is by-produced by a side reaction represented by the formula (2) which proceeds in the production stage of a chloroprene rubber which is industrially produced as shown by, for example, the following formula (1). Under the existing circumstances, there has been no effective use of the 1,2,3,4-tetrachlorobutane thus by-produced, and it has been generally made harmless by incineration or the like together with other chlorination by-products and discarded.

[Chem. 1]

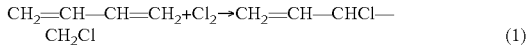

(1)

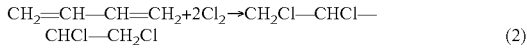

(2)

In the present invention, the 1,2,3,4-tetrachlorobutane which is discarded under the existing circumstances because of its no effective use can be used as a raw material for producing a fluorine-containing compound that is highly useful as, for example, an etching gas for semiconductors.

That is to say, in the production stage of a chloroprene rubber performed at present, after carrying out chlorination reaction of 1,3-butadiene and isomerization reaction, by-products produced by these reactions are separated by distillation to obtain 3,4-dichlorobutene-1 which is used for the production of a chloroprene rubber. Chloroprene is produced through dehydrochlorination from this 3,4-dichlorobutene-1. In the production step of a chloroprene rubber, 1,2,3,4-tetrachlorobutane which is a raw material in the present invention is contained in other chlorination by-products formed when 3,4-dichlorobutene-1 which is a raw material of a chloroprene rubber is produced.

After 3,4-dichlorobutene-1 is separated as above, 1,2,3,4-tetrachlorobutane which is a raw material in the production process of the present invention is separated from other chlorination by-products. In order to separate the 1,2,3,4-tetrachlorobutane from the other chlorination by-products which are by-produced when the 3,4-dichlorobutene-1 is produced, for example, a separation-purification method by distillation can be employed.

The separation-purification method by distillation has an advantage that a dl form and a meso form which are isomers of the 1,2,3,4-tetrachlorobutane can be individually separated and recovered.

As described above, the 1,2,3,4-tetrachlorobutane which is a raw material in the present invention can be obtained by separation-purification from the other chlorination by-products having been separated from 3,4-dichlorobutene-1. It can also be obtained by a method of chlorinating 3,4-dichlorobutene-1 which is a production intermediate of a chloroprene rubber.

In the method to obtain 1,2,3,4-tetrachlorobutane by chlorinating 3,4-dichlorobutene-1 which is a production intermediate of the chloroprene rubber, a product can be obtained with high purity.

In this method, high-purity 1,2,3,4-tetrachlorobutane having a purity of usually not less than 95% by mole, preferably not less than 98% by mole, can be obtained. By the use of such component with high purity, the purity of the resulting 1,2,3,4-tetrachlorohexafluorobutane is raised, and formation of by-products in the fluorination step is reduced to thereby make separation-purification easy.

As described above, In the 1,2,3,4-tetrachlorobutane used as a raw material in the present invention, isomers of a dl form and a meso form which are optical isomers are present. Of these isomers, the dl form has a melting point (mp) of not higher than 0° C. and a boiling point (bp) of about 213° C. The dl form is a liquid at room temperature. On the other hand, the meso form has a melting point of about 73° C. and a boiling point of about 213° C. The meso form is a white solid at room temperature.

Taking advantage of the differences in these physical properties, both of them can be separated.

In the present invention, it is desirable to use, as a raw material, 1,2,3,4-tetrachlorobutane mainly obtained by chlorination reaction of 3,4-dichlorobutene-1. In such 1,2,3,4-tetrachlorobutane, the concentration ratio of isomers is usually not less than 40% by mass for the dl form, and usually not more than 60% by mass for the meso form. By setting the content of the dl form in the raw material to not less than 40% by mass, heating or warming to dissolve the meso form in the dl form is scarcely required, so that possibility of occurrence of C—C cleavage or excessive fluorination is reduced, and decrease of selectivity or yield of the desired product is difficult to be induced.

In the process for producing a fluorine-containing compound such as 1,2,3,4-tetrachlorohexafluorobutane according to the present invention, a halogenated hydrocarbon compound such as the 1,2,3,4-tetrachlorobutane obtained as described above is brought into contact with fluorine gas in a liquid phase or in a solid-liquid coexistence state to produce a fluorine-containing compound. In this case, the fluorine gas and the halogenated hydrocarbon compound are brought into contact with each other without using a reaction solvent and without using a catalyst. The reaction solvent referred to herein is a substance other than the raw material used for the reaction and a reaction product obtained as a result of the reaction, said substance being liquid under the reaction conditions. Accordingly, for example, 1,2,3,4-tetrachlorobutane used as a raw material is not a reaction solvent but a reaction raw material in the present invention. And for example, liquid 1,2,3,4-tetrachlorohexafluorobutane produced by the reaction is not a reaction solvent but a reaction product in the present invention.

In the present invention, the halogenated hydrocarbon compound such as 1,2,3,4-tetrachlorobutane is fed as a raw material in a liquid state or in a solid-liquid coexistence state to a reaction apparatus without using a reaction solvent, and brought into contact with fluorine gas. A part of the halogenated hydrocarbon compound in a liquid state is a reaction raw material for this reaction and also functions as a reaction solvent, and fluorination reaction proceeds. Moreover, when the reaction product is liquid under the reaction conditions, a part of the fluorine-containing compound such as 1,2,3,4-tetrachlorohexafluorobutane obtained by, for example, a reaction at 40° C., functions as a reaction solvent. In the present invention, therefore, it is unnecessary to add, as a reaction solvent, a component other than a raw material and a reaction product to the reaction system.

In the fluorination step in the invention in which the halogenated hydrocarbon compound such as 1,2,3,4-tetrachlorobutane is caused to directly react with fluorine gas in a liquid phase or in a solid-liquid coexistence state in the absence of a solvent and a catalyst to produce a fluorine-containing compound, a reaction apparatus, such as an autoclave equipped with a stirring device and a gas blowing line (gas phase part and/or liquid phase part), can be used. Since the reaction apparatus, the feeding device, the stirring device, etc. are readily corroded by the introduced fluorine gas or the like, they are usually manufactured from anticorrosion materials. Examples of the anticorrosion materials include Teflon (registered trademark) lining of Inconel, Hastelloy, SUS and the like.

Into this reactor, the halogenated hydrocarbon compound such as the aforesaid 1,2,3,4-tetrachlorobutane is introduced as a reaction raw material. In the 1,2,3,4-tetrachlorobutane that is a typical example of the halogenated hydrocarbon compound, as described above, a dl form and a meso form are present as isomers. The dl form is liquid at room temperature, while the meso form is solid at room temperature. On this account, when the 1,2,3,4-tetrachlorobutane is used as a raw material, the concentration ratio of the isomers contained in the 1,2,3,4-tetrachlorobutane is set to such that the dl form is preferably not less than 40% by mass, more preferably not less than 60% by mass, and that the meso form is preferably not more than 60% by mass, more preferably not more than 40% by mass. When the dl form and the meso form are mixed in such ratio, the meso form is readily dissolved in the dl form to form a homogeneous liquid phase.

On the other hand, if the ratio of the meso form is increased, it becomes difficult to dissolve the meso form in the dl form to form a homogeneous liquid phase. When the ratio of the meso form is not less than 90% by mass, a solid-liquid coexistence state where the meso form that is solid and the dl form that is liquid coexist is formed. In the present invention, fluorination reaction proceeds without using a reaction solvent not only in the liquid phase but also in this solid-liquid coexistence state.

Next, an inert gas such as nitrogen gas is introduced into the reaction apparatus into which a raw material such as 1,2,3,4-tetrachlorobutane has been introduced, whereby a leakage test of the reaction apparatus is carried out. Besides, the inert (particularly oxygen-containing gas) are purged, and with stirring the raw material having been introduced into the reaction apparatus, fluorine gas is introduced to bring the halogenated hydrocarbon compound and the fluorine gas into contact with each other in a liquid phase or in a solid-liquid coexistence state.

In this case, the fluorine gas can be introduced into the gas phase part or can be introduced into the liquid phase part or the solid-liquid coexistence part. When 1,2,3,4-tetrachlorobutane is used as the halogenated hydrocarbon compound that is a raw material, the fluorine gas is preferably introduced into the liquid phase part in the case that the content of the dl form contained therein is not less than 50% by mass, while the fluorine gas is preferably introduced into the gas phase part in the case that the content of the meso form is not less than 50% by mass.

As the fluorine gas introduced into the reaction apparatus, diluted fluorine gas obtained by diluting with an inert diluent gas is usually used. The concentration of the fluorine gas in the diluted fluorine gas is set to usually not less than 30% by volume, preferably 30 to 70% by volume. By setting the lower limit of the fluorine gas in the diluted fluorine gas to 30% by volume as above, the reaction rate of the fluorination reaction can be controlled in a proper range. And by setting the upper limit to 70% by volume, C—C cleavage in the halogenated hydrocarbon compound during the fluorination reaction is prevented, and thereby increase of a low-boiling component and progress of side reaction such as formation reaction of an excess fluorination product can be inhibited.

The diluent gas which is used for preparing the diluted fluorine gas used herein is a gas inert to fluorine gas and inert to a raw material used for the reaction and a reaction product obtained as a result of the reaction. Examples of such inert gases include nitrogen gas, helium gas, argon gas and neon gas. These gases can be used alone or in combination. Particularly in the present invention, it is desirable to use nitrogen gas which is readily available and inexpensive.

In the present invention, the method to dilute the fluorine gas with the inert gas as described above is not specifically restricted. It is possible that the fluorine gas is fed to the reaction apparatus together with the diluent gas in given ratios to be diluted in the reaction apparatus. Taking into consideration homogeneity of the diluted fluorine gas, it is preferable that the diluent gas and the fluorine gas are mixed before the fluorine gas is introduced into the reaction apparatus and then introduced into the reaction apparatus in a homogeneous state.

In the production of a fluorine-containing compound in the present invention, the reaction temperature is set in the range of usually −10 to 70° C., preferably 0 to 60° C. In order to carry out production of a fluorine-containing compound without using a reaction solvent and without using a catalyst in the present invention, the halogenated hydrocarbon which is a raw material is allowed to be in a liquid state or a solid-liquid coexistence state and brought into contact with the diluted fluorine gas, while setting the reaction temperature in the aforementioned temperature range. By allowing the raw material to be in a liquid state or a solid-liquid coexistence state and bringing it into contact with the fluorine gas in the above temperature range, fluorination reaction favorably proceeds even if a catalyst is not used. Moreover, since the upper limit of the reaction temperature is not high, cleavage reaction of carbon-carbon bond in the halogenated hydrocarbon compound which is a raw material is difficult to proceed, and by-production of a low-molecular weight substance is very little, so that the fluorine-containing compound can be produced very efficiently.

In the process for producing a fluorine-containing compound of the present invention which is carried out under the above temperature conditions, the reaction pressure is set in the range of usually 0.1 to 2.0 MPa, preferably 0.1 to 1.0 MPa. If this reaction condition is lower than 0.1 MPa, progress of the reaction is slow. If the reaction pressure exceeds 2.0 MPa, a reaction apparatus having a pressure-resistant strong structure becomes necessary, and an increase in cost of the product is induced.

By performing operations under the above reaction conditions in the process for producing a fluorine-containing compound of the invention, the raw material and the fluorine gas exhibit high activities, and even if a reaction solvent and a reaction catalyst are not used, fluorination reaction of the halogenated hydrocarbon compound smoothly proceeds. Fluorine (specifically diluted fluorine gas) having been introduced into the reaction apparatus under such conditions is consumed with the progress of the reaction, and the pressure in the reaction apparatus is lowered.

When the pressure in the reaction apparatus is lowered with the consumption of the fluorine gas, an inert gas may be introduced into the reaction apparatus to temporarily discharge the fluorine gas from the reaction apparatus, and then a diluted fluorine gas may be introduced in the same manner as above, whereby the reaction can be continued. As the fluorine gas introduced at this time, the same diluted fluorine gas as the diluted fluorine gas first introduced can be used, but the ratio of fluorine gas in the diluted gas can be increased with the progress of the reaction. For example, a method of stepwise raising the fluorine gas concentration, such as a method wherein the concentration of the fluorine gas in the diluted fluorine gas introduced for the second time is set at 40% by volume provided the concentration of the fluorine gas in the diluted fluorine gas first introduced is 30% by volume, is adoptable.

By carrying out fluorination reaction of the halogenated hydrocarbon in the above manner, the yield of the resulting fluorine-containing compound is usually not less than 50% by mole based on the charged raw material.

In the reaction product thus obtained, not only the fluorine-containing compound that is the desired product but also an unreacted raw material, a low-molecular weight substance due to side reaction of C—C cleavage, an excess fluoride, etc. are sometimes contained, but these components can be readily separated by distillation.

Through such distillation step, the purity of the resulting fluorine-containing compound, particularly 1,2,3,4-tetrachlorohexafluorobutane, can be raised to preferably not less than 95% by mole.

EXAMPLES

The present invention is described with reference to the following examples, but the present invention is in no way limited to those examples.

Raw Material Example 1

By chlorination reaction of 1,3-butadiene industrially produced, 3,4-dichlorobutene-1 and 1,4-dichlorobutene-2 were mainly generated. The 1,4-dichlorobutene-2 was made into 3,4-dichlorobutene-1 by isomerization reaction. The 3,4-dichlorobutene-1 was obtained by distillation separation.

The resulting component was analyzed by gas chromatography, and as a result, the purity was 99.3% by mole.

The 3,4-dichlorobutene-1 was subjected to chlorination reaction with chlorine gas to obtain 1,2,3,4-tetrachlorobutane. The resulting component was analyzed by gas chromatography. The results of the analysis are shown below.

1,2,3,4-Tetrachlorobutane, purity: 99.1% by mol

The ratios of isomers in the 1,2,3,4-tetrachlorobutane were as follows.

dl form:meso form=46% by mass:54% by mass

Raw Material Example 2

The 1,2,3,4-tetrachlorobutane obtained in <Raw Material Example 1> was cooled (−20° C.) to precipitate a meso form, then it was separated and an analysis was performed by gas chromatography. The results are shown below.

1,2,3,4-Tetrachlorobutane, purity: 99.0% by mole

The ratios of isomers in the 1,2,3,4-tetrachlorobutane after separation of the precipitated meso form were as follows.

dl form:meso form=91% by mass:9% by mass

Raw Material Example 3

The meso form, which had been precipitated by cooling, then separated and recovered in <Raw Material Example 2>, was recrystallized with a solvent. This component was analyzed by gas chromatography. The results are shown below.

1,2,3,4-Tetrachlorobutane, purity: 98.7% by mol

The ratios of isomers in the 1,2,3,4-tetrachlorobutane were as follows.

dl form:meso form=3% by mass:97% by mass

Example 1

Into a reactor made of SUS 304 (Teflon (registered trademark) lining) and having an internal volume of 200 ml, 30 g (0.153 mol) of 1,2,3,4-tetrachlorobutane (dl form/meso form=46/54) obtained in the above Raw Material Example 1 was charged, and nitrogen gas was introduced at 1.0 MPa to perform a leakage test. Thereafter, with purging the nitrogen gas, inert matters in the reactor were replaced and the reactor temperature was maintained at 15° C. while stirring.

Then, prior to introduction into the reactor, fluorine gas and nitrogen gas were mixed to obtain 50 vol % fluorine gas, and it was introduced into the reactor from a liquid phase part through a gas feeding pipe provided on the reactor at a reaction pressure of 0.5 MPa to initiate reaction. After 2 hours, the nitrogen gas was mainly purged from a gas discharging pipe provided on the reactor, then operations of 50 vol % fluorine gas, reaction and gas discharging were repeated. Finally, the reaction temperature was raised to 40° C. to complete the reaction.

The amount of the introduced fluorine gas was about 0.92 mol. Thereafter, the inside of the reactor was replaced with nitrogen gas, and the reaction product was recovered and analyzed by gas chromatography. The result of the analysis is shown below.

1,2,3,4-Tetrachlorohexafluorobutane, yield: 69.8% by mole

As apparent from the result, 1,2,3,4-tetrachlorohexafluorobutane that is a targeted product can be obtained in a high yield in the absence of a solvent and a catalyst.

Example 2

Into a reactor made of SUS 304 (Teflon (registered trademark) lining) and having an internal volume of 200 ml, 40 g (0.204 mol) of 1,2,3,4-tetrachlorobutane (dl form/meso for m=91/9) obtained in the above Raw Material Example 2 was charged. Nitrogen gas was introduced at 1.0 MPa to perform a leakage test. Thereafter, with purging the nitrogen gas, inert matters in the reactor were replaced, and then the reactor temperature was maintained at 10° C. while stirring.

Then, prior to introduction into the reactor, fluorine gas and nitrogen gas were mixed to obtain 35% fluorine gas, and it was introduced into the reactor from a liquid phase part through a gas feeding pipe provided in the reactor at a reaction pressure of 0.5 MPa to initiate reaction. After 3 hours, the nitrogen gas was mainly purged from a gas discharging pipe provided on the reactor, then operations of introduction of 35% fluorine gas, reaction and gas discharging were repeated. Finally, using 50% fluorine gas, the reaction temperature was raised to 40° C. to complete the reaction.

The amount of the introduced fluorine gas was about 1.22 mol. Thereafter, the inside of the reactor was replaced with nitrogen gas, and the reaction product was recovered and analyzed by gas chromatography. The result of the analysis is shown below.

1,2,3,4-Tetrachlorohexafluorobutane, yield: 74.2% by mol

Example 3

Into a reactor made of SUS 304 (Teflon (registered trademark) lining) and having an internal volume of 200 ml, 30 g (0.153 mol) of 1,2,3,4-tetrachlorobutane (dl form/meso for m=3/97) obtained in the above Raw Material Example 3 was charged, and nitrogen gas was introduced at 1.5 MPa to perform a leakage test. Thereafter, with purging the nitrogen gas, inert matters in the reactor were replaced, and then the reactor temperature was maintained at 15° C. while stirring.

Then, prior to introduction into the reactor, fluorine gas and nitrogen gas were mixed to obtain 40% fluorine gas, and it was introduced into the reactor from a gas phase part through a gas feeding pipe provided on the reactor at a reaction pressure of 0.8 MPa to initiate reaction. After 3 hours, the pressure decreased to about 0.3 MPa because the fluorine gas was consumed, then 100% fluorine gas was introduced through a gas feeding pipe provided on the reactor to set the pressure at 0.8 MPa, and operations of reaction and feeding of 100% fluorine were repeated. Finally, the reaction was completed under the conditions of a reaction pressure of 1.0 MPa and a reaction temperature of 40° C.

The amount of the introduced fluorine gas was about 0.96 mol. Thereafter, the reactor was replaced with nitrogen gas, and the reaction product was recovered and analyzed by gas chromatography. The result of the analysis is shown below.

1,2,3,4-Tetrachlorohexafluorobutane, yield: 64.8% by mole

As apparent from the result, 1,2,3,4-tetrachlorohexafluorobutane can be obtained in the absence of a solvent even using a meso form that is solid at room temperature.

INDUSTRIAL APPLICABILITY

According to the present invention, a fluorine-containing compound such as 1,2,3,4-tetrachlorohexafluorobutane can be readily produced by bringing a halogenated hydrocarbon compound such as 1,2,3,4-tetrachlorobutane into contact with fluorine gas in a liquid phase or in a solid-liquid coexistence state in the absence of a solvent and a catalyst to cause them to react with each other.

According to the present invention, further, a fluorine-containing compound such as 1,2,3,4-tetrachlorohexafluorobutane which is a targeted product can be readily separated with high purity because a reaction solvent and a reaction catalyst are not used.

The 1,2,3,4-tetrachlorobutane, which is a specific exemplary compound of the halogenated hydrocarbon compound used as a raw material in the present invention, is a substance formed by side reaction in the production step of a chloroprene rubber. The 1,2,3,4-tetrachlorobutane is a substance which has been so far made harmless and discarded because there is no effective use thereof. The present invention has an advantage that the 1,2,3,4-tetrachlorobutane conventionally having no effective use can be used as, for example, a raw material component of an etching gas for semiconductors, and its industrial applicability is extremely high.

The invention claimed is:

1. A process for producing 1,2,3,4-tetrachlorohexafluorobutane, comprising causing 1,2,3,4-tetrachlorobutane to react with fluorine gas in a liquid phase or in a solid-liquid coexistence state in the absence of a solvent and a catalyst,
    wherein the 1,2,3,4-tetrachlorobutane is mainly obtained by a chlorination reaction of 3,4-dichlorobutene-1,
    in the 1,2,3,4-tetrachlorobutane obtained by the chlorination reaction of the 3,4-dichlorobutene-1, a dl form which is an optical isomer is contained in an amount of not less than 40% by mass, and
    the reaction temperature of the reaction is in the range of 0 to 60° C.

2. The process for producing 1,2,3,4-tetrachlorohexafluorobutane as claimed in claim 1, wherein the reaction pressure of the reaction is in the range of 0.1 to 2.0 MPa.

3. The process for producing 1,2,3,4-tetrachlorohexafluorobutane as claimed in claim 1, wherein the fluorine gas is diluted with a diluent gas and then introduced into a reaction apparatus.

4. The process for producing 1,2,3,4-tetrachlorohexafluorobutane as claimed in claim 3, wherein the concentration of the fluorine gas in the diluted fluorine gas is not less than 30% by volume.

5. The process for producing 1,2,3,4-tetrachlorohexafluorobutane as claimed in claim 3, wherein the diluent gas is at least one inert gas selected from the group consisting of nitrogen gas, helium gas, argon gas and neon gas.

6. The process for producing 1,2,3,4-tetrachlorohexafluorobutane as claimed in claim 4, wherein the diluent gas is at least one inert gas selected from the group consisting of nitrogen gas, helium gas, argon gas and neon gas.

* * * * *